(12) United States Patent
Swartz et al.

(10) Patent No.: US 8,865,441 B2
(45) Date of Patent: Oct. 21, 2014

(54) EFFICIENT CELL-FREE HYDROGEN PRODUCTION

(75) Inventors: James R. Swartz, Menlo Park, CA (US); Phillip Smith, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/246,542

(22) Filed: Sep. 27, 2011

(65) Prior Publication Data

US 2012/0077242 A1    Mar. 29, 2012

Related U.S. Application Data

(60) Provisional application No. 61/404,238, filed on Sep. 28, 2010.

(51) Int. Cl.
*C12P 3/00* (2006.01)

(52) U.S. Cl.
CPC ....................................... *C12P 3/00* (2013.01)
USPC ........................................... 435/168; 435/7.1

(58) Field of Classification Search
None
See application file for complete search history.

(56) References Cited

U.S. PATENT DOCUMENTS 7,351,563 B2    4/2008    Swartz et al.

OTHER PUBLICATIONS

Zhang et al. (Plos One, May 2007, No. 5, pp. 1-6).*
Li et al. (J. Bacteriology, 2008, vol. 190, No. 3, pp. 843-850).*
Smith et al. (Int'l J. of Hydrogen Energy, vol. 37, pp. 2977-2983).*
Wood et al. (Microbial Biotech., 2008, vol. 1, No. 1, pp. 30-39).*
Zhang et al. (Plos ONE, vol. 2, No. 5, May 2007, pp. 1-6).*
Schmidt et al. (Frontiers in Neuroenergetics, vol. 1, Mar. 2009, pp. 1-10).*
Aslund et al. (PNAS, vol. 96, pp. 6161-6165, 1999).*
Shaw et al. (J. Bacteriology, 2009, vol. 191, No. 20, pp. 6457-6464).*
Smith; et al., "Generation of hydrogen from NADPH using an [FeFe] hydrogenase", International Journal of Hydrogen Energy (2011), XXX, 1-7.
Woodard; et al., "Enzymatic production of biohydrogen", Nature (2000), 405:1014-1015.
Zhang; et al., "High-Yield Hydrogen Production from Starch and Water by a Synthetic Enzymatic Pathway", PLoS ONE (2007), 5:e456, 6 pages.

* cited by examiner

*Primary Examiner* — Hope Robinson
(74) *Attorney, Agent, or Firm* — Bozicevic, Field & Francis LLP; Pamela J. Sherwood

(57) ABSTRACT

Cell-free synthesis of hydrogen from glucose and cellulosic hydrolysates is provided. Bacterial cells are modified to express high levels of (i) active [FeFe] hydrogenase; (ii) ferredoxin; and (iii) ferredoxin-NADP-reductase (FNR). The cells are then lysed and the lysate is combined with substrate during a production phase, where $H_2$ is produced. The substrate is typically a sugar, e.g. glucose, cellulose hydrolysates, fructose, and the like, including pentose sugars capable of entering the bacterial pentose phosphate cycle. The reaction mixture may be further supplemented with one or more of niacin as a precursor to nicotinamide; a nuclease, particularly a ribonuclease, to break down nucleic acids and generate adenine; and iodoacetamide to inactivate the normal cellular glycolytic pathway and thus maximize conversion yields.

11 Claims, 9 Drawing Sheets

FIGURE 3
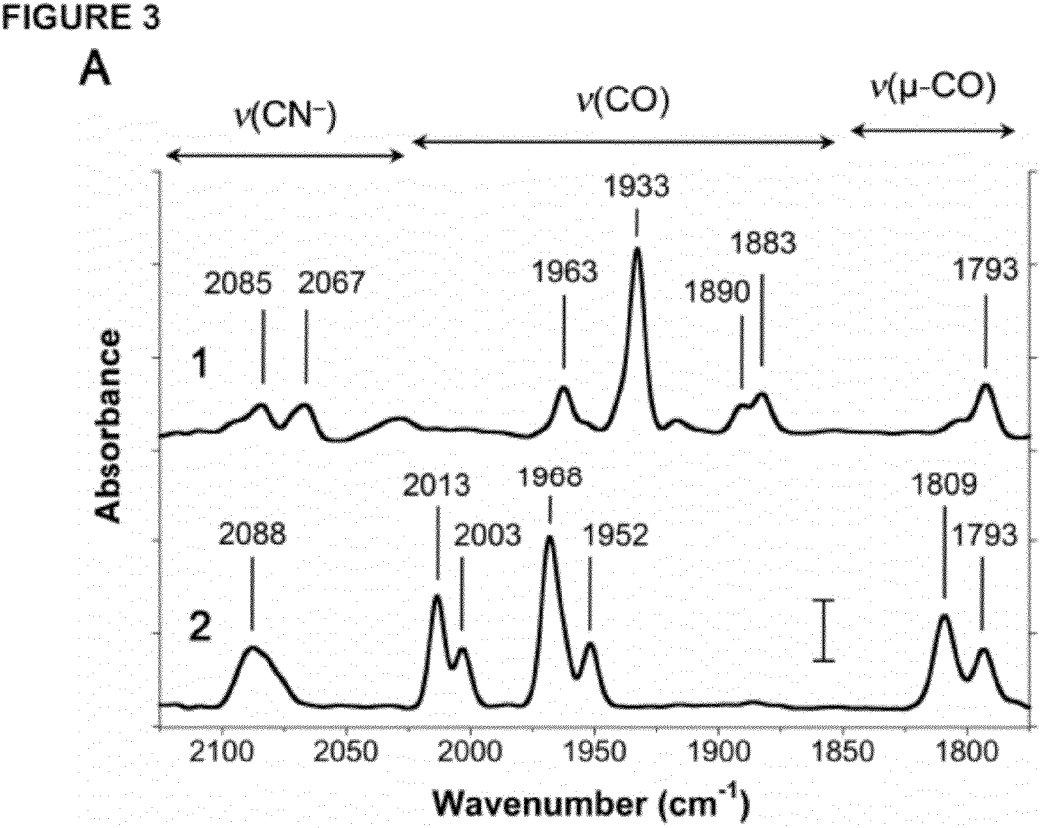
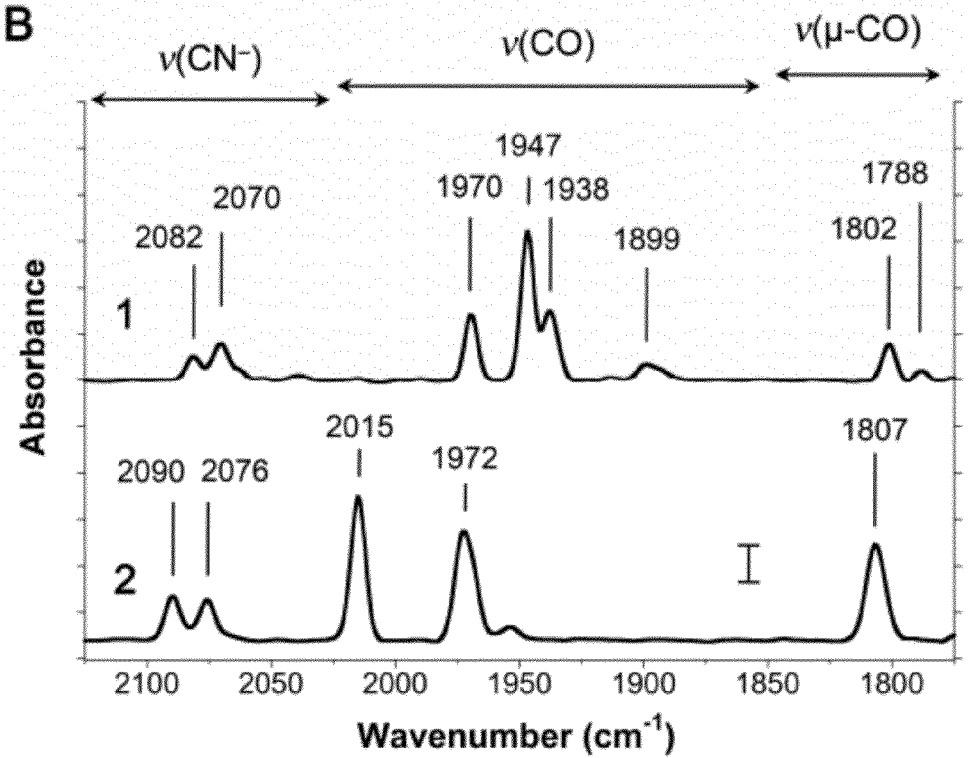

FIGURE 4
A
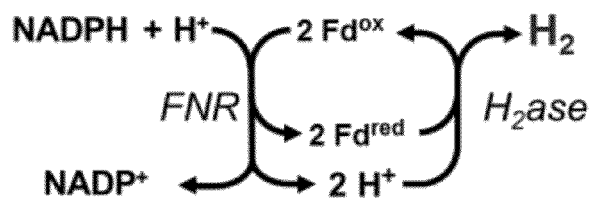
B
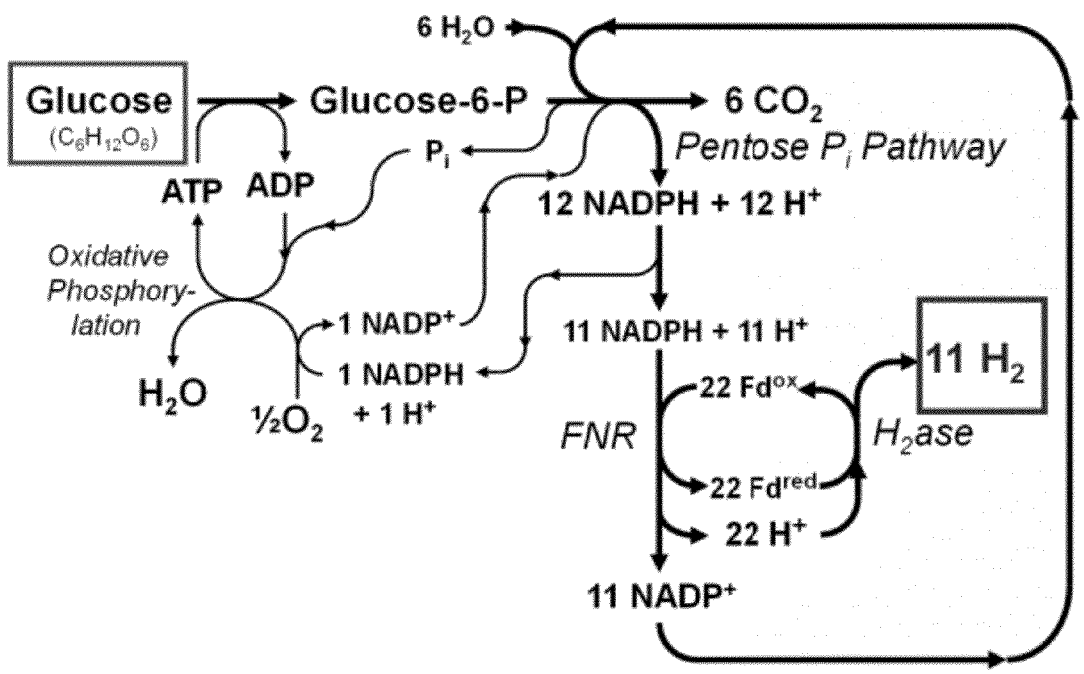

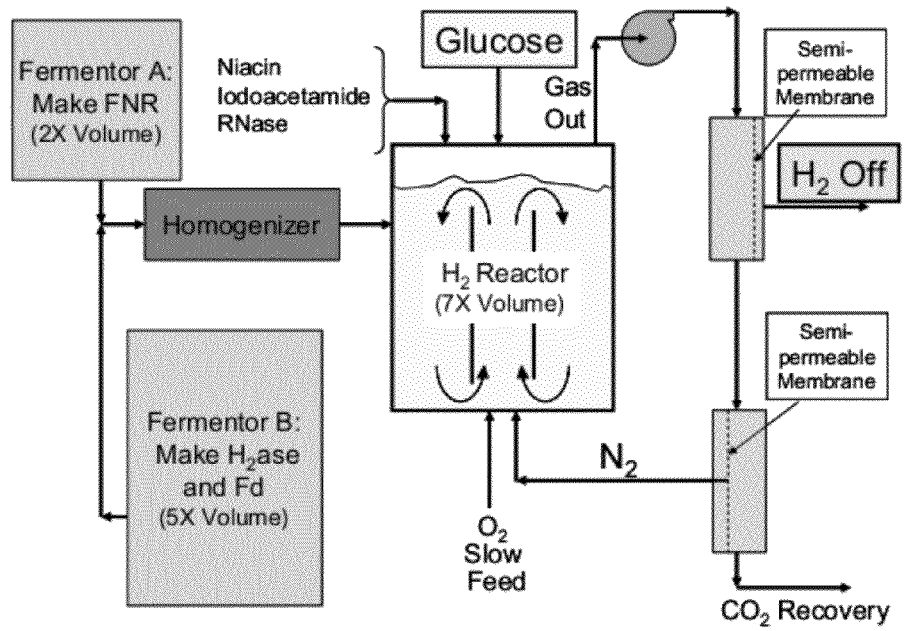

B $$\left(\frac{100 \text{ g EtOH}}{L}\right)\left(\frac{1}{60 \text{ hr}}\right)\left(\frac{0.025 \text{ MJ}}{\text{g EtOH}}\right) = 0.04 \text{ MJ/L-hr}$$

$$\left(\frac{86 \text{ μmole H}_2\text{ase}}{L}\right)\left(\frac{5 \text{ μmoles H}_2}{\text{mole H}_2\text{ase} \cdot \text{sec}}\right)\left(\frac{3600 \text{ sec}}{\text{hr}}\right)\left(\frac{\text{mole}}{10^6 \text{ μmole}}\right)\left(\frac{2 \text{ g H}_2}{1 \text{ mole H}_2}\right)\left(\frac{0.13 \text{ MJ}}{\text{g H}_2}\right) = 0.40 \text{ MJ/L-hr}$$

C

| Vessel | [FNR] (μM) | [Fd] (μM) | [H$_2$ase] (μM) |
|---|---|---|---|
| Fermentor A | 505 | --- | --- |
| Fermentor B | --- | 1166 | 120 |
| H$_2$ Reactor | 144 | 833 | 86 |

# EFFICIENT CELL-FREE HYDROGEN PRODUCTION

Current traditional energy technologies rely on fossil fuels. Their most significant limitations are the depletion of limited fossil fuel reservoirs, thus, making this a non-sustainable technology, and the net generation of $CO_2$ and other greenhouse gases, thereby affecting the global climate in a fundamental and uncontrollable manner. Hydrogen gas is a renewable energy source that does not evolve the "greenhouse gas" $CO_2$ in combustion, liberates large amounts of energy per unit weight in combustion, and is easily converted to electricity by fuel cells.

The US current market for hydrogen is very large and is likely to grow. For example, US agriculture uses about 20 million tons of $NH_3$ fertilizer every year, and each ton of ammonia fertilizer requires about 34 million Btu worth of natural gas to provide the hydrogen for the reduction of gaseous nitrogen. The petrochemical industry also uses very large quantities of hydrogen, produced exclusively from fossil fuels with large releases of $CO_2$.

Thus, current sources of hydrogen often rely on fossil fuels as input material, and conventional means for industrial-scale $H_2$ production such as steam reformation of natural gas fall short of the environmental criteria now needed for sustainable fuels and chemicals. The use of hydrogen as a large scale fuel therefore depends, in part, on developing new hydrogen sources.

For a variety of reasons, a large fraction of recent public and private funding has been focused on the production and use of cellulosic biomass. This situation provides an important opportunity for technology that uses cellulosic hydrolysates as feedstocks to produce hydrogen. One path of particular interest is biological hydrogen production from biomass, enabled by genetically engineered microbes that express hydrogenases—enzymes that catalyze the reversible reduction of protons into $H_2$. If this hydrogen could be produced from cellulosic crops grown on marginal lands, the resulting ammonia fertilizer would be produced with minimal new $CO_2$ release and would also help to improve the productivity of neighboring land devoted to food crops.

The present invention relates to the production of hydrogen as a sustainable local feedstock from glucose and cellulosic hydrolysates using cell-free technology to provide precise control over metabolic fluxes while minimizing toxic effects of cellulosic byproducts.

Literature citations. Woodward et al. (2000) Enzymatic production of biohydrogen. Nature 405:1014-1015; Zhang et al. (2007) High-yield hydrogen production from starch and water by a synthetic enzymatic pathway. PLoS ONE 2: e456.

SUMMARY OF THE INVENTION

Compositions and methods are provided for the cell-free synthesis of hydrogen from glucose and cellulosic hydrolysates. In the methods of the invention, bacterial cells are modified to express high levels of (i) active [FeFe] hydrogenase; (ii) ferredoxin; and (iii) ferredoxin-NADP-reductase (FNR). These proteins may be referenced herein collectively as $H_2$ pathway proteins. The $H_2$ pathway proteins may be expressed in a single cell or in separate cells, usually the ferredoxin and FNR are expressed in separate cells. Desirably at least one of the bacterial cells also expresses cytochrome D oxidase.

The cells are then lysed and the lysate, which may be a crude lysate, is combined with substrate during a production phase, where $H_2$ is produced. The substrate is typically a sugar, e.g. glucose, cellulose hydrolysates, fructose, and the like, including pentose sugars capable of entering the bacterial pentose phosphate cycle. The reaction mixture may be further supplemented with one or more of niacin as a precursor to nicotinamide; a nuclease, particularly a ribonuclease, to break down nucleic acids and generate adenine; and iodoacetamide to inactivate the normal cellular glycolytic pathway and thus maximize conversion yields. Preferred reaction conditions are substantially anaerobic, however a slow $O_2$ feed sufficient exhaust the $O_2$ by glucose phosphorylation is utilized in some embodiments.

In some embodiments of the invention, the fuel value productivity will be at least about 0.1 MJ $L^{-1}$ $hr^{-1}$, at least about 0.25 MJ $L^{-1}$ $hr^{-1}$, at least about 4 MJ $L^{-1}$ $hr^{-1}$, or more. For each mole of glucose, 5 or more, 7.5 or more, 10 or more moles of $H_2$ may be produced.

Hydrogenases of interest include, without limitation, [FeFe] hydrogenases that primarily catalyze $H_2$ evolution, e.g. *Chlamydomonas reinhardtii* [FeFe]-hydrogenase; *Clostridium pasteurianum* hydrogenase; *Megasphaera elsdenii* hydrogenase; derivatives; variants; homologs; mutants; and the like. The hydrogenases are usually synthesized in a cell expressing at least one hydrogenase accessory protein. In some embodiments, the cells are initially grown under aerobic conditions, and switched to anaerobic conditions for expression of the hydrogenase.

Ferredoxins of interest include, without limitation, *Clostridium pasteurianum* ferredoxin; *Synechocystis* ferredoxin, *E. coli* ferredoxin, *Spinacia oleracea* ferredoxin; *Anabaena* ferredoxin, derivatives; variants; homologs; mutants; and the like. Included, without limitation, are $Fe_2S_2$, and $Fe_4S_4$ ferredoxins. A candidate ferredoxin may be assayed for $H_2$ production with a hydrogenase and/or FNR of interest, and may be evolved to optimize activity. The ferredoxin may be synthesized in a cell with the hydrogenase.

Ferredoxin-NADP-reductase, EC 1.18.1.2, may be obtained from any suitable source, including *E. coli*, *Anabaena* sp., and the like, including FNR from photosynthetic organisms such as higher plants, e.g. spinach. FNR may be expressed in a cell other than the cell expressing hydrogenase and/or ferredoxin.

In another aspect, the invention provides an in vitro cell-free system for the synthesis of $H_2$, the system containing cell lysates, a sugar, and proteins: (i) active [FeFe] hydrogenase; (ii) ferredoxin; (iii) ferredoxin-NADP-reductase (FNR); NADP. Desirably cytochrome D oxidase is also present. Phosphate and nucleotides may be obtained endogenously from the cell extract by enzymes present in the extract or added to the extract.

Other features and advantages of the invention will be apparent from the detailed description, and from the claims.

BRIEF DESCRIPTION OF THE DRAWINGS

(FIG. 1A) Optical density at 600 nm (shown on a logarithmic scale) of cultures during aerobic (*) and anaerobic (*) growth phases for cells containing the pACYCDuet-1-hydGX-hydEF and pET-21(b) shydA1*-Strep-tag II plasmids. The pH of culture media (*) was also measured. Data for cultures cells containing the pET-21(b) shydA-Strep-tag II vector instead of pET-21(b) shydA1*-Strep-tag II were similar and are not shown. (FIG. 1B) Cell lysate-based hydrogenase activities (μmol MV reduced·$min^{-1}$·$mg^{-1}$ total protein) for active CpI (*) and HydA1 hydrogenase (*) were determined using the methyl viologen reduction assay. Data are the average for n=3 cultures examined±SEM. (FIG. 1C) SDS-PAGE analysis for the soluble fractions of final cell lysates after the anoxic co-expression of HydA1 or Cpl and the HydEFG maturases. The molecular weight markers (Lane 1) are from the Mark12™ protein ladder (Invitrogen). Soluble cell lysate protein content for *E. coli* strain BL21(DE3) ΔiscR following expression of no heterologous proteins from recombinant DNA plasmids (Lane 2); co-expression of only the HydE, HydF, and HydG maturases (Lane 3); co-expression of HydEFG and HydA1-Strep-tag II (Lane 4); and co-expression of HydEFG and Cpl-Strep-tag II (Lane 5).

FIGS. 3A-3B Fourier transform infrared spectra of heterologous [FeFe] hydrogenases produced in *E. coli*. Infrared spectra are for 100-200 μM of the (A) HydA1 and (B) Cpl hydrogenases. Both enzymes were examined [1] in their as-isolated state as well as [2] following treatment with exogenous CO. Vibrational energies (in cm$^{-1}$) for the H-cluster CO and CN-ligands are indicated in each spectrum. The wavenumber ranges for terminal ON-(γCN—)), terminal CO (γ(CO)), and bridging CO (γ(μ-CO)) vibrational modes are shown above the spectra. Scale bars shown at 1870 cm$^{-1}$ represent a difference of 0.5 milliabsorbance units.

FIGS. 4A-4B Metabolic pathways for efficient production of hydrogen from glucose.

FIGS. 6A-6B. Process flow diagram for an industrial process to produce hydrogen from glucose. Sample protein concentrations are shown and a sample calculation is also drawn comparing volumetric productivity of the representative process to that of an ethanol production process.

Figure 1:
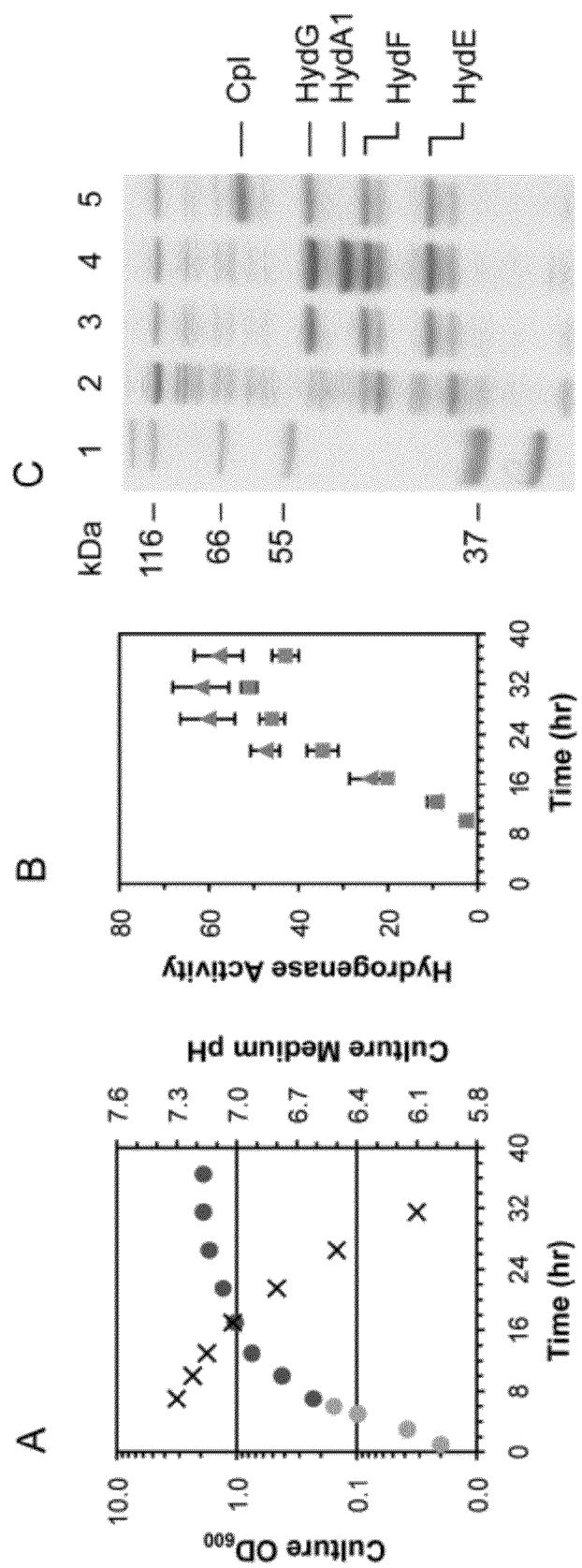
FIGS. 1A-1C. *E. coli* growth and anaerobic expression of heterologous active [FeFe] hydrogenases. All data are for cultures of *E. coli* strain BL21(DE3) ΔiscR, and both iron and cysteine were included in the growth medium.

Example 9. Hydrogen production from glucose using a cell-lysate combined with purified enzymes

DETAILED DESCRIPTION OF THE EMBODIMENTS

Compositions and methods are provided for the cell-free synthesis of hydrogen from glucose and cellulosic hydrolysates. The invention consists of an enzymatic pathway composed of the following proteins: (1) Ferredoxin NADPH Reductase (FNR), (2) Ferredoxin, and (3) [FeFe] Hydrogenase; this pathway can be combined with any source of reducing equivalents delivered by NADPH. In the embodiments of the invention, these proteins are overexpressed to high levels in one or more cell cultures; following overexpression, the cultures are lysed (homogenized) and combined as necessary to facilitate hydrogen production from simple sugars in a bioreactor. In the bioreactor, the enzyme pathway functions together with an active pentose-phosphate pathway (PPP) in the *E. coli* extract to transfer electrons from the sugars to the [FeFe] hydrogenase. The hydrogenase combines the electrons with available protons to produce hydrogen, which is collected. Nicotinamide adenine dinucleotide phosphate (NADPH) functions as an important intermediate to transfer electrons; additional NADPH is optionally made in the bioreactor by supplementing the extracts with one or more of niacin (a common vitamin and nicotinamide precursor) and nuclease (to provide a source of adenine by breakdown of nucleic acids already in the cell extract). Additionally, iodoacetamide may be added to inactivate the normal glycolytic pathway of the bacterial cells to avoid loss of the sugars through conversion to other metabolic products and to thereby maximize conversion yields. Various C6 and C5 sugars find use, e.g. glucose, fructose, xylose, etc., and may be obtained from starch, from cellulose, hemicellulose or from combinations thereof.

FIG. 4 illustrates the overall metabolic scheme for this proposal. Glucose is first converted to glucose 6-P using ATP generated by oxidative phosphorylation. The glucose 6-P enters the pentose phosphate pathway where it is converted to 6 CO$_2$'s while providing 12 NADPH's. One NADPH is used to provide the ATP for glucose phosphorylation, and the other 11 are used for reducing equivalents for hydrogen production. The enzyme ferredoxin-NADP$^+$ reductase (FNR) catalyzes the transfer of electrons from NADPH to ferredoxin (Fd), in contrast to previous approaches. The use of FNR and ferredoxin allows the use of a highly active enzyme, the [Fe—Fe] Cpl hydrogenase from *Clostridium pasteurianum*. Note that the metabolic flow shown in FIG. 4 accounts for all of the atoms described by the overall reaction shown below. The ATP, NADP, and ferredoxin are all recycled.

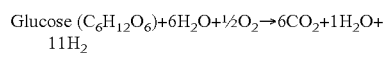
Glucose (C$_6$H$_{12}$O$_6$)+6H$_2$O+½O$_2$→6CO$_2$+1H$_2$O+ 11H$_2$

In some embodiments, the process will utilize cell extracts in which the enzymes have been overexpressed. This enables cost effective production since no purification is required and several enzymes are provided by one organism. The hydrogenase and ferredoxin are both oxygen sensitive and are Fe—S proteins, and may be conveniently expressed in one organism with aerobic growth switching to an anaerobic expression period. A second fully aerobic fermentation may be used to express FNR and to provide the other enzymes required, including those for oxidative phosphorylation and glucose phosphorylation. The enzymes that constitute the pentose phosphate pathway are present in the extracts and do not require overexpression

DEFINITIONS

Hydrogenase. Hydrogenases catalyse the reversible oxidation/reduction of molecular hydrogen (H$_2$) and play a vital role in anaerobic metabolism. Metal containing hydrogenases are subdivided into three classes: Fe—Fe hydrogenases, Ni—Fe hydrogenases, and Fe hydrogenases. Hydrogen oxidation is coupled to the reduction of electron acceptors such as oxygen, nitrate, sulphate, carbon dioxide and fumarate, whereas proton reduction (H$_2$ evolution) is coupled to molecules such as ferredoxin. The methods of the invention may be applied to any of the Fe—Fe hydrogenases that accept electrons from ferredoxin.

In one embodiment, the term "hydrogenase" as used herein refers to an enzyme that meets one or more of the criteria provided herein. Using these criteria, one of skill in the art can determine the suitability of a candidate enzyme for use in the methods of the invention. Many enzymes will meet multiple criteria, including two, three, four or more of the criteria, and some enzymes will meet all of the criteria. The terms "hydrogenase" can refer to a full length enzyme or fragment thereof with the capability of catalyzing hydrogen oxidation/reduction.

Hydrogenases of the invention include enzymes having at least about 20% sequence identity at the amino acid level, more usually at least about 40% sequence identity, and preferably at least about 70% sequence identity to one of the following hydrogenases: *Chlamydomonas reinhardtii* iron-iron-hydrogenase (GENBANK® accession AY055756); *Clostridium pasteurianum* hydrogenase (GENBANK® accession AAA23248.1); *Megasphaera elsdenii* hydrogenase (GENBANK® accession AF120457); *Desulfovibrio vulgaris* hydrogenase (GENBANK® accession CAA26266.1). For example, see Forestier et al. (2003) Eur. J. Biochem. 270 (13), 2750-2758; Meyer et al. (1991) Biochemistry 30:9697-9704; Voordouw et al., (1985) Eur. J. Biochem. 148:515-520; Atta et al. (2000) Biochim Biophys Acta. 1476 (2):368-71; Fauque et al. (1988) FEMS Microbiol. Rev. 4, 299-344; Cammack et al. (1994) Methods Enzymol. 243, 43-68; and de Lacey et al. (1997) J. Am. Chem. Soc. 119, 7181-7189, each herein incorporated by reference.

Homology-based identification (for example, by a PILEUP sequence analysis) of enzymes can be routinely performed by those of skill in the art upon contemplation of this disclosure to identify those suitable for use in the methods of the present invention. Such enzymes are usually produced in microorganisms, particularly bacteria. Hydrogenases of the invention also include an enzyme belonging to the enzyme classifications EC 1.12.7.2 and EC 1.12.2.1.

The nucleic acid sequences encoding the above hydrogenases may be accessed from public databases as previously cited. Identification of additional hydrogenases is accomplished by conventional screening methods of DNA libraries or biological samples for DNA sequences having a high degree of similarity to known hydrogenase sequences.

Iron-iron hydrogenase. The hydrogenases containing no other metal than Fe and containing an active site H-cluster consisting of a 4Fe-4S subcluster joined by a cysteine residue to a 2Fe-2S cluster are called Fe—Fe hydrogenases ([Fe—Fe] Hases). Two families of Fe—Fe Hases have been described. Cytoplasmic, soluble, monomeric Fe—Fe Hases are found in strict anaerobes such as *Clostridium pasteurianum* and *Megasphaera elsdenii*. They are extremely sensitive to inactivation by $O_2$ and catalyze both $H_2$ evolution and uptake. Periplasmic, heterodimeric (Fe—Fe) Hases from *Desulfovibrio* spp., can be purified aerobically but catalyze mainly $H_2$ oxidation.

3-D structures of $H_2$ evolving (Fe—Fe) Hase I from *Clostridium pasteurianum* (CpI) and *Desulfovibrio desulfuricans* uptake hydrogenase (DdH) are known. The overall structure of CpI resembles a mushroom consisting of four domains: the large active site domain forms "cap" and three smaller domains form "stem". The "stem" domains bind four iron-sulphur clusters and are termed FS4A-FS4B, FS4C and FS2. The N-terminal FS2 domain binds a [$Fe_2S_2$] cluster and shares the overall fold with plant-type ferredoxins. The FS4A-FS4B domain is adjacent to the active site domain; it contains two [$Fe_4S_4$] clusters and has the overall fold similar to that of bacterial type ferredoxins. The FS4C domain is placed between the FS2 and FS4A-FS4B domains and consists of two α-helices linked by a loop that binds a single [$Fe_4S_4$] cluster via one His and three Cys residues. The large subunit of DdH lacks FS4C and FS2 clusters and corresponding domains. The small subunit of DdH has an unusual fold consisting of alternating random coil and four α-helices that form a "belt" around the large subunit.

The active site domain of the (Fe—Fe) Hases contains an unusual Fe—S center termed the H-cluster. H-cluster consists of the [$Fe_4S_4$] subcluster bridged via the Cys thiolate to the [$Fe_2$] (binuclear iron-iron) subcluster. The two iron-iron atoms are designated Fe1 and Fe2 (proximal and distal with respect to the [$Fe_4S_4$] subcluster) and are ~2.6 Å apart. With the exception of the bridging Cys, the diiron-iron subcluster is coordinated by non-protein ligands. In CpI, both iron-iron atoms are octahedrally coordinated to five CO/CN ligands, three S ligands and one water molecule. Fe1 and Fe2 are bridged by two S atoms and one CO or CN ligand. The two bridging sulphurs themselves are bridged by atom(s) of unknown identity. In DdH, Fe1 and Fe2 are bridged by a small molecule that has been modelled as 1,3-propanedithiol (PDT). Fe1 is octahedrally coordinated while Fe2 has square pyramidal coordination geometry.

In some embodiments of the invention, the iron-iron hydrogenase is derived from a *Clostridium* species, for example as shown in the appended sequences of SEQ ID NO:1, 2, 3, 4 and 5, in which the targeted residues are underlined. Hydrogenases of interest include, without limitation, those found in the species *Clostridium botulinum; Clostridium tyrobutyricum; Clostridium perfringens; Clostridium butyricum; Clostridium saccharobutylicum; Clostridium novyi; Clostridium pasteurianum; Clostridium acetobutylicum; Clostridium cellulovorans; Clostridium paraputrificum; Clostridium kluyveri* DSM 555; *Clostridium papyrosolvens*, etc. and the related species *Alkaliphilus metalliredigens, Eubacterium acidaminophilum, Anaerocellum thermophilum, Caldicellulosiruptor saccharolyticus* etc.

$O_2$ tolerance. As used herein, the term $O_2$ tolerance refers to the ability of a hydrogenase enzyme to retain activity in the presence of molecular oxygen. As is known in the art, even trace levels of $O_2$ can be sufficient to inactivate known hydrogenases. Enzymes that have been mutated to increase tolerance may have at least about 10% activity, at least about 20% activity, at least about 30% activity or more after a solution of the protein is exposed to 0.01 atm $O_2$. The enzymes may be more resistant to $O_2$ when the enzyme is present in a microbial host cell (relative to a solution).

As used herein, "in vitro reaction" refers to a reaction performed in a controlled environment (e.g., an experimental environment or an environment outside a living organism).

As used herein, "cell-free" refers to a non-living system, e.g., in vitro or ex vivo systems containing cellular components. Sources for the components of cell-free systems include cell extracts and lysates, usually a crude cell lysate. As used herein a crude cell lysate comprises the lysate of a population of cells, which is substantially free of intact cells; and which is usually not subjected to enrichment techniques such as chromatography, dialysis, and the like. Such a cell lysate may or may not be clarified by such means as centrifugation or filtration. Cell-free systems are able to reconstitute cellular reactions, e.g., enzymatic and metabolic pathways. A cell lysate, usually a crude cell lysate, is obtained from cells expressly engineered to synthesize one or more proteins of interest, which results in the generation of a compound of $H_2$.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A "coding sequence" or a sequence which "encodes" a selected polypeptide, is a nucleic acid molecule which is transcribed (in the case of DNA) and translated (in the case of mRNA) into a polypeptide, for example, in a cell-free polypeptide synthesis reaction; or in vivo when placed under the control of appropriate regulatory sequences (or "control elements"). The boundaries of the coding sequence are typically determined by a start codon at the 5' (amino) terminus and a translation stop codon at the 3' (carboxy) terminus. A transcription termination sequence may be located 3' to the coding sequence. Other "control elements" may also be associated with a coding sequence.

"Operably linked" refers to an arrangement of elements wherein the components so described are configured so as to perform their usual function. Thus, a given promoter that is operably linked to a coding sequence (e.g., a reporter expression cassette) is capable of effecting the expression of the coding sequence when the proper enzymes are present. The promoter or other control elements need not be contiguous with the coding sequence, so long as they function to direct the expression thereof. For example, intervening un-translated yet transcribed sequences can be present between the promoter sequence and the coding sequence and the promoter sequence can still be considered "operably linked" to the coding sequence.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning and expression vehicles, as well as integrating vectors.

"Purified polynucleotide" refers to a polynucleotide of interest or fragment thereof which is essentially free, e.g., contains less than about 50%, preferably less than about 70%, and more preferably less than about 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

A "polypeptide" is used in it broadest sense to refer to a compound of two or more subunit amino acids, amino acid analogs, or other peptidomimetics. The subunits may be linked by peptide bonds or by other bonds, for example ester, ether, etc. As used herein, the term "amino acid" refers to either natural and/or unnatural or synthetic amino acids, including glycine and both the D or L optical isomers, and amino acid analogs and peptidomimetics.

Extract organism. As described above, the coding sequence for one or more $H_2$ pathway proteins are present or introduced into the source organism, and may be present on a replicable vector or inserted into the source organism genome using methods well-known to those of skill in the art. Such vector sequences are well known for a variety of bacteria. The expression vector may further comprise sequences providing for a selectable marker, induction of transcription, etc.

The coding sequences are operably linked to a promoter sequence active in the organism. Promoters are untranslated sequences located upstream (5') to the start codon of a structural gene (generally within about 100 to 1000 bp) that control the transcription and translation of particular nucleic acid sequence. Promoters may be constitutive or inducible, where inducible promoters initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to protein-encoding DNA by removing the promoter from the source DNA, e.g. by PCR amplification of the sequence, etc. and inserting the isolated sequence into the vector. Both the native hydrogenase promoter sequence and many heterologous promoters may be used for expression, however, heterologous promoters are preferred, such as T7, as they generally permit greater transcription and higher yields. Promoters suitable for use with prokaryotic hosts include the β-lactamase and lactose promoter systems; alkaline phosphatase; a tryptophan (trp) promoter system; an arabinose promoter system; and hybrid promoters such as the tac promoter. However, other known bacterial and bacteriophage promoters are suitable. Their nucleotide sequences have been published, thereby enabling a skilled worker operably to ligate them to DNA encoding the $H_2$ pathway proteins.

Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*.

Host cells are transfected and preferably transformed with the above-described expression or cloning vectors and cultured in conventional nutrient media modified as appropriate for inducing promoters, selecting transformants, and preparing extracts as set forth in the Examples.

Sugar. As used herein, the term refers to a number of carbohydrates, such as monosaccharides, disaccharides, oligosaccharides, and polysaccharides, usually pentose or hexose sugars or polymers thereof. Monosaccharides that find use include, without limitation, fructose, arabinose, lyxose, ribose, xylose, ribulose, xylulose, deoxyribose, allose, altrose, glucose, mannose, gulose, idose, galactose, talose. Disaccharides may include sucrose, lactose, maltose, etc. Polysaccharides may include starches, glycogen, cellulose, pectin, peptidoglycan, lipopolysaccharides, capsules, exopolysaccharides, and the like. Sugars may be phosphorylated, e.g. glucose-6-phosphate, etc. Sugars may be included in the reaction mix at a concentration sufficient to provide energy for $H_2$ evolution, e.g. from about 1 mM to about 1000 mM, and may be about 5 mM, 10 mM, 25 mM, 50 mM, 75 mM, 100 mM, 250 mM, 500 mM, 750 mM, 1000 mM.

Reaction mix: as used herein refers to a reaction mixture capable of catalyzing the synthesis of $H_2$ from sugar, which sugar may be a phosphorylated or non-phosphorylated sugar. The reaction mixture comprises extracts from bacterial cells, and the synthesis is performed under substantially anaerobic conditions. The volume percent of extract in the reaction mix will vary, where the extract is usually at least about 10% of the total volume; more usually at least about 20%; and in some instances may provide for additional benefit when provided at least about 50%; at least about 60%; or at least 75% of the total volume. In certain industrial applications the volume percent of extract may be around about 90% or higher. The reaction mixture may be further supplemented with one or more of niacin, nicotinamide, NAD, etc., usually at a concentration of from about 0.1 mM to 1 mM, e.g. at about 0.3 mM, about 0.5 mM, about 0.75 mM, etc. as a precursor or source of NAD; a nuclease, particularly a ribonuclease, which may be used at a conventional dose for example from about 0.5 µg/ml to about 50 µg/ml, to break down nucleic acids and generate adenine; and an agent to inactivate the endogenous microbial cell glycolytic pathway and thus maximize conversion yields.

Useful inactivating agents include iodoacetamide, N-ethyl maleimide, iodoacetate, N-iodoacetyl-N'-(5-sulfonic-1-naphthyl)ethylene diamine, etc., as known in the art; especially those compounds including iodoacetamides, maleimides, benzylic halides and bromomethylketones. The concentration of inactivation agent and length of time for the reaction will be determined by the specific compound that is chosen. The inactivation agent is added at a concentration that substantially eliminates the endogenous cellular glycolytic pathway activity. As an example, where the inactivation agent is iodoacetamide, it may be added at a concentration of from about 10 to about 50 µM, and incubated from between 15 to 60 minutes.

Before describing the present invention in detail, it is to be understood that this invention is not limited to particular formulations or method parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

Production Methods

High yield production of a product of interest is accomplished by providing a cell in which $H_2$ pathway proteins are expressed. During cell culture it may be desirable to control the components of the growth medium of the cells in order to avoid exposure of the hydrogenase to conditions that affect activity, e.g. exposure to $O_2$ and the like. Generally the pathway components are produced in two or more different cells. For production purposes, a lysate of the cell is utilized. Cells are lysed by any convenient method that substantially maintains enzyme activity, e.g. sonication, French press, and the like as known in the art. The lysate may be fractionated, particulate matter spun out, etc., or may be used in the absence of additional processing steps. The cell lysate may be further combined with substrates, co-factors and such salts, buffers, etc. as are required for activity, and may be treated with iodoacetamide or a similar agent. Substrates will usually include glucose or another suitable sugar, a source of nicotinamide, and a source of ATP or adenine.

Lysates of cells of different genetic backgrounds, e.g. previously altered or genetically engineered, or species, or that are prepared by different strategies can be mixed and simultaneously or sequentially used in a bioprocess with the cell lysate of the invention. The lysate can be free or immobilized, and can be reused or disposed at each stage of the process.

The reactions may utilize a large scale reactor, small scale, or may be multiplexed to perform a plurality of simultaneous syntheses. Continuous reactions will use a feed mechanism to introduce a flow of reagents, and may isolate the end-product as part of the process. Batch systems are also of interest, where additional reagents may be introduced over time to prolong the period of time for active synthesis or to limit the production of side products. A reactor may be run in any mode such as batch, extended batch, semi-batch, semi-continuous, fed-batch and continuous, and which will be selected in accordance with the application purpose.

The reactions may be of any volume, either in a small scale, usually at least about 1 ml and not more than about 15 ml, or in a scaled up reaction, where the reaction volume is at least about 15 ml, usually at least about 50 ml, more usually at least about 100 ml, and may be 500 ml, 1000 ml, or greater up to many thousands of liters of volume. Reactions may be conducted at any scale.

Various salts and buffers may be included, where ionic species are typically optimized with regard to product production. When changing the concentration of a particular component of the reaction medium, that of another component may be changed accordingly. Also, the concentration levels of components in the reactor may be varied over time. The adjuster of the thiol/disulfide oxidation/reduction potential may be dithiothreitol, ascorbic acid, glutathione and/or their oxidized forms. Other adjusters of the general redox potential may also be used.

In a semi-continuous operation mode, the reactor may be operated in dialysis, diafiltration batch or fed-batch mode. A feed solution may be supplied to the reactor through the same membrane or a separate injection unit. The gaseous products, hydrogen and $CO_2$, may be removed in a stream of an anoxic carrier gas such as nitrogen. The reactor may be stirred internally or by proper agitation means, including by gas sparging. The amount of hydrogen produced can be determined using gas flow meters and any instrument that measures the % $H_2$ in the gas, such as a gas chromatograph. The hydrogen can then be removed from the $CO_2$ and carrier gas by any convenient means, as known in the art.

Figure 7:
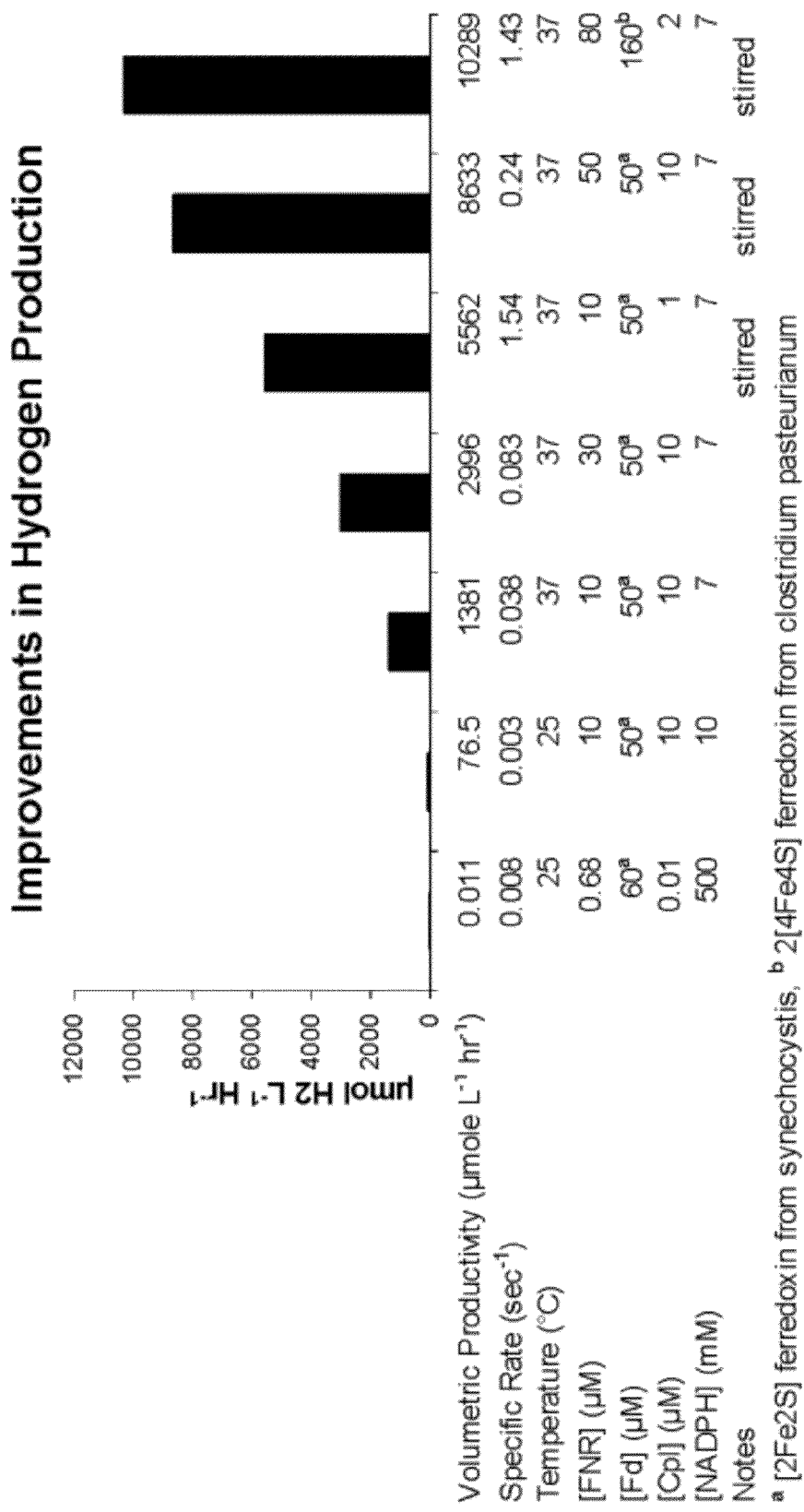
FIG. 7. Improvements in Hydrogen Production

A simplified flow diagram for the industrial scale production of hydrogen from glucose is shown in FIG. 7. A single set of large cell extract production fermenters (for example, a 60,000 liter and a 150,000 liter fermenter) would supply the enzyme mix (cell extract) for several (most likely 3 to 5) hydrogen bioreactors. *E. coli* grows rapidly requiring roughly 12 hours to reach high cell density (about 200 g/l) and another 8 to 10 hours to express the enzymes required for hydrogen production. This cell suspension may be passed directly through a high pressure homogenizer and into a hydrogen production vessel. Assuming the cell extract would retain acceptable activity for 3 days, one cell production fermenter would supply three hydrogen bioreactors. The $N_2$ required for gas circulation in the hydrogen bioreactors may be obtained from the off-gas of the aerobic fermentation during a microaerobic incubation. By feeding air at a lower rate, the dissolved oxygen concentration will go essentially to zero to induce the high affinity cytochrome oxidase (cytochrome d oxidase) needed for the oxidative phosphorylation in the hydrogen reactor. During this period, the organism will strip all of the oxygen from the air, replacing it with $CO_2$ which will be removed to leave essentially pure nitrogen.

After the cells are lysed, e.g. by a single pass through the high pressure homogenizer, the resultant cell extract may be directly transferred into the hydrogen bioreactor, treated with iodoacetamide to inactivate the EMP pathway and supplemented with NADP and FAD as required. Antifoaming agents may be added, and the oxygen-free nitrogen obtained from the microaerobic fermentation can be circulated through the bioreactor to harvest the hydrogen. The hydrogen may be removed with nanoporous inorganic membrane devices.

The hydrogen thus obtained may be transferred directly to a local consumer such as an ammonia fertilizer producer, a cement producer, or a petrochemical plant. Alternatively, storage and transportation technology may be utilized for broader distribution. The $CO_2$ may be removed by semi-permeable membrane, and the like, and can be sequestered or sold.

In the hydrogen bioreactors, glucose concentrations and hydrogen production will be monitored to adjust glucose feed rates to optimal levels and to decide when the reactor needs to be recharged with new cell extract. (The waste extract could then be sold as fertilizer for local farms.) Nitrogen gas would be circulated to maintain a low hydrogen partial pressure to encourage rapid hydrogen formation. A small feed of air would be added at the gas inlet of each reactor to provide the oxygen required for ATP generation. This rate would also be controlled at the optimal level based on metabolite measurements.

As explained above, the technology is deployable at large scale, can easily be implemented by building production facilities near cellulosic biomass processing centers, provides a clean fuel, and also includes provisions for capturing the released $CO_2$. By providing hydrogen from renewable resources, very large volume $CO_2$ emissions would be avoided, particularly for the production of nitrogen fertilizers.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications that might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Example 1

We describe an improved *Escherichia coli*-based expression system capable of producing 8-30 mg of purified, active [FeFe] hydrogenase per liter of culture, volumetric yields at least 10-fold greater than previously reported. Specifically, we overcame two problems associated with other in vivo production methods: low protein yields and ineffective hydrogenase maturation. The addition of glucose to the growth medium enables anaerobic respiration during hydrogenase expression, which substantially increases total yields. Also, we combine iron and cysteine supplementation with the use of an *E. coli* strain upregulated in iron-sulfur cluster protein accumulation. These measures dramatically improve in vivo hydrogenase activation. Two hydrogenases, HydA1 from *Chlamydomonas reinhardtii* and HydA (Cpl) from *Clostridium pasteurianum*, were produced with this improved system and subsequently purified. Biophysical characterization and FTIR spectroscopic analysis of these enzymes indicate that they harbor the H-cluster and catalyze $H_2$ evolution with rates comparable to those of enzymes isolated from their respective native organisms. The production system we describe will facilitate basic hydrogenase investigations as well as the development of new technologies that utilize these prolific $H_2$-producing enzymes. These methods can also be extended for producing and studying a variety of oxygen-sensitive iron-sulfur proteins as well as other proteins requiring anoxic environments.

Hydrogenases catalyze the redox interconversion of protons and hydrogen gas ($2H^+ + 2e^- <>H_2$) using unique transition metal cofactors by which the enzymes are classified. Since [FeFe] hydrogenases more rapidly and preferentially evolve $H_2$ than [NiFe] hydrogenases, they are more desirable for $H_2$ production technologies. Unfortunately, these prolific $H_2$ producing enzymes are also easily inactivated by oxygen. The [FeFe] hydrogenase active site cofactor, termed the H-cluster, is a complex iron sulfur cluster that is stabilized by carbon monoxide and cyanide ligands as well as a dithiol bridging molecule. H-cluster assembly and active hydrogenase expression require at least three accessory proteins called the HydE, HydF, and HydG maturases, yet the biosynthetic pathway for the H-cluster is also poorly understood. Furthermore, most work with hydrogenases and their maturases must be done in strict anaerobic environments since the reduced nature of the H-cluster and accessory iron sulfur clusters (ISCs) makes them susceptible to damage by $O_2$ oxidation. Research groups have overcome these challenges and have used hydrogenases for energy conversion at the laboratory scale in several different applications. Protein complexes attached to solid-state devices have evolved $H_2$ using electrons activated by light. Photoelectrochemical fuel cells with hydrogenases adsorbed to cathodic carbon electrodes have preferentially evolved $H_2$ and perform similarly to fuel cells that use platinum catalysts. Also, synthetic metabolic pathways assembled with purified enzymes have converted sugars to $H_2$ and $CO_2$ at high yields. Despite the successful development of these hydrogenase technologies, their commercial realization and sustainability will require large quantities of active protein. Various microbial systems have been engineered for producing native and heterologous [FeFe] hydrogenases [14-20], but active enzyme yields are generally less than 1 mg·$L^{-1}$ of culture. Also, few recombinant DNA tools exist for effective overexpression of proteins in organisms that naturally harbor [FeFe] hydrogenases.

*Escherichia coli* has several advantages that make it desirable for hydrogenase production. The bacterium does not contain a native [FeFe] hydrogenase to compete for biosynthetic precursors and complicate analytical measurements, it is capable of anaerobic respiration, and heterologous expression techniques for this microbe are well established. Active hydrogenase production using *E. coli* systems has been demonstrated, with total yields comparable to the best reported. However, specific activities of purified hydrogenases from these systems are significantly lower than activities of hydrogenases isolated from their native hosts, likely because of incomplete enzyme maturation.

We describe the high-yield production of active [FeFe] hydrogenases using the HydEFG maturases native to *Shewanella oneidensis* along with *E. coli* BL21(DE3) ΔiscR, a strain previously engineered for improved synthesis of iron-sulfur (Fe—S) proteins. Following expression with our optimized protocol, both the *C. reinhardtii* HydA1 and *C. pasteurianum* CpI hydrogenases were isolated by STREP-TACTIN® affinity chromatography and characterized using activity assays and FTIR spectroscopy.

Results

Recombinant Protein Expression Concurrent with Anaerobic Respiration. Co-expression of the [FeFe] hydrogenases and the HydEFG maturases was induced under strict anoxic conditions at an optical density ($OD_{600}$) of ~0.4. To facilitate anaerobic respiration, glucose (0.5% w/v) and the electron acceptor fumarate (25 mM) were added to the complex growth medium. Aerobic growth rates were exponential (0.45 $hr^{-1}$), while anaerobic growth rates were linear and eventually ceased after 24 hr at final $OD_{600}$ measurements ranging from 1.5 to 3.0 (FIG. 1A). Substrate limitations and acetate accumulation may have contributed to the slowed anoxic growth. Without glucose addition, the culture density did not increase during the anaerobic incubation period. This lack of growth resulted in a lower mass of cells accumulated, which thus decreased the total amount of hydrogenase produced per culture volume.

Active hydrogenase levels were determined in samples taken during the anaerobic respiration period by measuring the methyl viologen reduction activities of cell lysates. This assay for hydrogenase-catalyzed $H_2$ uptake enabled us to identify the conditions for optimal active enzyme production. For both the HydA1 and CpI hydrogenases, maximal activities were observed after 20-24 hr of anaerobic incubation (FIG. 1B), and expression levels of the four heterologous proteins were similar based on SDS-PAGE analysis (FIG. 1C). Increased rates of cell death accompanied by protein degradation could explain the modest decrease in activity after 24 hr, as anoxic growth appeared to cease at this time. Only minimal amounts of methyl viologen reduction (less than 1% of the maximal activities) were observed when either the hydrogenase alone or only the three maturases were expressed. Thus, methyl viologen reduction could be specifically attributed to active [FeFe] hydrogenase in the cell lysates, and not the HydEFG maturases or native *E. coli* [NiFe] hydrogenases.

Figure 2:
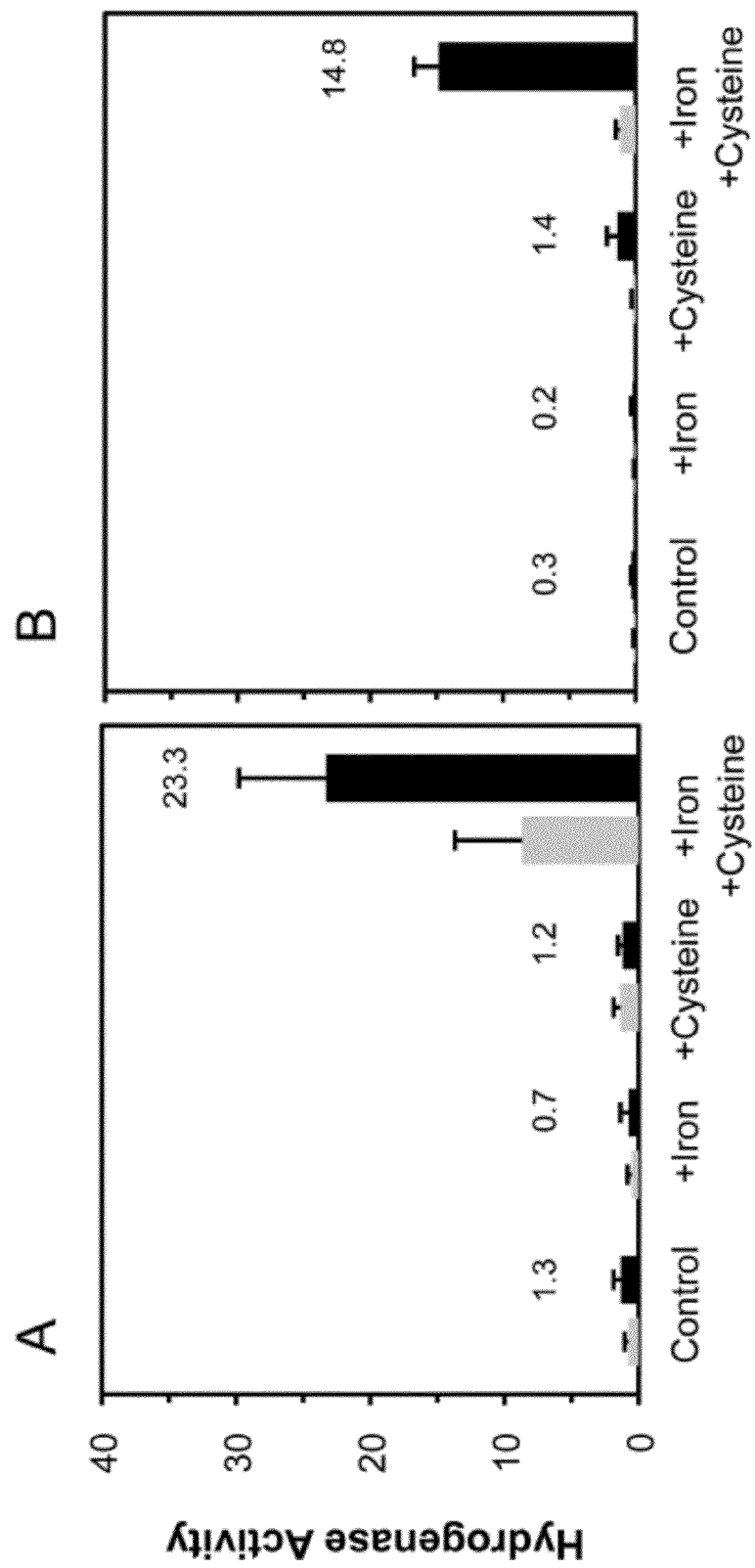
FIGS. 2A-2B. Effects of iron and cysteine supplementation as well as the iscR deletion on active hydrogenase expression. Iron (2 mM ferric ammonium citrate) and cysteine (2 mM) were added to cultures as indicated. Methyl viologen reducing activities (μmol MV reduced·min$^{-1}$·mg$^{-1}$ total protein) of active [FeFe] hydrogenase in cell lysates from *E. coli* strains BL21(DE3) (gray bars) and BL21(DE3) ΔiscR (black bars). Hydrogenase activities were measured after 16-18 hrs of anaerobic (A) HydA1 expression and (B) Cpl expression. Hydrogenase activities are shown on a logarithmic scale and are the average for n=2 cultures±SEM.
Figure 5:
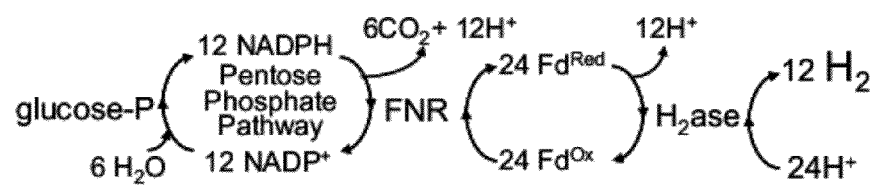
FIG. 5: Enzymatic pathway from glucose-P to hydrogen.

[FeFe] hydrogenases and each of the three maturases require ISCs in order to function. Recombinant overexpression of the four Fe—S proteins likely creates increased demand for ISC assembly. We therefore investigated the benefits of supplementing potentially limiting substrates as well as using the mutant ΔiscR strain engineered for improved production of proteins harboring ISCs. Expression with the ΔiscR strain improved active hydrogenase production 2-10 fold, with a greater benefit for CpI production (FIG. 2). Addition of both iron (2 mM ferric ammonium citrate) and cysteine (2 mM) to the culture medium resulted in a further 5-10 fold increase in hydrogenase activity. Neither additive individually improved hydrogenase activation to the same level, although cysteine supplementation led to a moderate improvement in active CpI expression when using the ΔiscR strain. The cooperative effect of iron and cysteine suggests that both substrates are limiting when overexpressing proteins harboring ISCs.

Biophysical Characterization of Purified [FeFe] Hydrogenases. HydA1 and CpI were expressed using the conditions identified for maximal hydrogenase activities, and we subsequently isolated the enzymes to high purity with Strep-Tactin affinity chromatography. The elution fractions containing active hydrogenase were confirmed using the methyl viologen reduction assay as well as by SDS-PAGE analysis. Generally, 70-90% of the total activity present in the cell lysates was recovered in the elution fractions. The purification yields for HydA1 and CpI were 30 mg·$L^{-1}$ of culture and 8 mg·$L^{-1}$ of culture, respectively.

Both specific activities and protein-bound iron content were determined for the purified HydA1 and CpI enzymes. $H_2$ uptake rates as well as $H_2$ evolution rates are comparable for the two proteins, albeit higher for CpI in all cases. We also used the purified *Synechocystis* ferredoxin PetF (50 μM) instead of methyl viologen as the electron donating substrate, and we estimated a $K_m$ of 20 μM for this [2Fe-2S] ferredoxin with CpI when using sodium dithionite (DTH) as the source of electrons. Using PetF, however, supported significantly lower $H_2$ evolution rates compared to methyl viologen. Both HydA1 and CpI contained ~70% of the maximum amount of iron (6 and 20 iron atoms are expected for HydA1 and CpI, respectively).

FTIR Spectroscopic Analysis of Isolated [FeFe] Hydrogenase. Fourier Transform IR spectroscopy was used to analyze the purified HydA1 (FIG. 3A) and CpI hydrogenases (FIG. 3B) in both the as-isolated state as well as following treatment with exogenous CO. Spectra for both as-isolated hydrogenases clearly show peaks representing CN— and CO vibrational stretches, indicating the presence of fully assembled H-clusters. Based on previous reports for each of these enzymes as well as other [FeFe] hydrogenases, these spectra also indicate that the as-isolated hydrogenases have a mixture of H-clusters in both the oxidized ($H_{ox}$) and reduced ($H_{red}$) states. The presence of DTH in the elution buffer was essential to prevent hydrogenase inactivation during purification, and this was likely the cause for the mixture of H-cluster redox states. The CO inhibition studies confirmed the presence of the H-cluster cofactors, as the CO and $CN^-$ vibrational modes shifted as expected after exogenous CO binding to the H-cluster.

By implementing several changes for heterologous [FeFe] hydrogenase expression, we achieved HydA1 and CpI yields more than 10-fold higher than previously reported for these enzymes. Furthermore, the purified hydrogenases are highly active and contain a properly assembled H-cluster based on in vitro enzymatic activities and FTIR spectroscopic analyses. Enabling concurrent anaerobic respiration and T7 RNA polymerase induction was essential for increased heterologous protein production. In the absence of anoxic cell growth (i.e. incubation without glucose added to the medium), anaerobic hydrogenase and maturase accumulation levels were noticeably lower, as indicated by both hydrogenase activity assays and SDS-PAGE analysis. This decrease in protein expression could be expected since translation is energy intensive due to the high entropic demands, and the rates of ATP synthesis are dramatically reduced under non-respiring conditions.

Previous studies using *E. coli* as an expression host for heterologous [FeFe] hydrogenase production reported specific activities much lower than those measured for the same protein purified from its native host, likely due to incomplete hydrogenase maturation as well as possible loss of activity during purification. The CpI and HydA1 enzymes produced with our optimized system have specific activities similar to those of the respective wild-type enzymes isolated from their native hosts. Like the [FeFe] hydrogenases, the HydEFG maturases also require ISCs. Thus, the benefits of the engineered ΔiscR strain along with iron and cysteine supplementation could be expected since not one, but four Fe—S proteins must be overexpressed. The more pronounced benefit of the ΔiscR strain for active CpI expression (FIG. 2B) might be explained by the enzyme's requirement for N-terminal ISCs. Unlike the algal HydA1 hydrogenase, CpI has three additional [4Fe-4S] clusters and one additional [2Fe-2S] cluster that participate in electron transfer to the H-cluster cofactor. As transcription of the E. coli isc operon is deregulated in the ΔiscR strain, higher expression of the corresponding native ISC proteins likely enhances the assembly, installation, and/or repair of these four accessory ISCs. The benefit of cysteine supplementation for active CpI expression in the ΔiscR strain further supports this hypothesis, as increased in vivo levels of the cysteine desulfurase IscS may improve cysteine utilization for ISC biosynthesis.

With our methods and a single purification step, we obtained greater than 70% recovery of the in vivo hydrogenase activity. Nevertheless, we identified several factors that affected the overall efficacy of the purification process such as the necessity for DTH during protein purification. When buffers did not contain fresh DTH, both HydA1 and CpI more rapidly deactivated, in agreement with previously reported observations. We also used a commercial lysis buffer (BugBuster Master Mix) to produce the lysates as this approach is simpler (given the anaerobic requirements) than alternative methods such as sonication and homogenization. High-yield expression was also beneficial for efficient recovery, since hydrogenase concentrations in the lysates (estimated to be 5-25 µM) are then higher than the $K_d$ for Strep-tag II:Strep-Tactin adsorption (1 µM). The affinity tag location was another important factor as observed in other studies. While the presence of a C-terminal affinity tag did not seem to negatively affect the solubility or catalytic properties of the hydrogenases, we could not produce soluble CpI with an N254 terminal affinity tag. Moreover, HydA1 with an N-terminal affinity tag had a 50% lower specific activity, as indicated by both activity assays. Traditional methods for isolating HydA1 without an affinity tag have combined multiple purification steps, and the majority of the hydrogenase activity (80-90%) was lost during the procedures. Also, immobilized metal ion affinity chromatography (IMAC) could cause detrimental interactions between protein metal clusters and the resin, and high salts are generally used to recover the bound protein. Strep-Tactin affinity chromatography may also be more favorable for purifying metalloproteins compared to multi-step chromatography or IMAC. The Strep-Tactin approach involves a single chromatography step for efficient recovery of pure protein. Moreover, buffer exchanges are not required to deplete high salt concentrations, which allows for facile sample preparation such as concentrating the isolated active hydrogenase for FTIR spectroscopic analysis.

The production of two active, but structurally different [FeFe] hydrogenases using heterologous maturases illustrates the versatility of this expression system. Infrared spectroscopic data confirm the presence of CO and CN-ligands, indicating that both HydA1 and CpI contain an intact H-cluster identical to that of the protein produced in the native organisms and assembled by the native maturases. Despite the evolutionary diversity of [FeFe] hydrogenases, H-cluster biosynthesis and hydrogenase maturation appear to be highly conserved. Our results also underscore the modularity of the microbial world and the potential for dramatic evolutionary change through DNA exchange and mutation. It thus seems likely that the HydEFG maturases from S. oneidensis could also activate other [FeFe] hydrogenases of interest (e.g. hydrogenases from Thermotoga maritima and Desulfovibrio vulgaris). One advantage of using the S. oneidensis maturases is the similarity between Shewanella and Escherichia. For example, high yields and soluble expression of HydE, HydF, and HydG were observed, even without codon optimizing the maturase genes (FIG. 10).

The effectiveness of E. coli for inducible expression of heterologous proteins along with the variety of commercial recombinant DNA expression tools make this organism more desirable than others (e.g. Clostridia) for the large-scale production of hydrogenases for a variety of applications. In this work, we illustrate this advantage via the facile production of hydrogenase for IR spectroscopic analysis. Such analytical techniques generally require large quantities of hydrogenase per sample (>500 µg) at concentrations greater than 5 $mg \cdot mL_{-1}$. With our system, sufficient quantities of HydA1 and CpI hydrogenase for multiple IR spectroscopic measurements can be obtained from a single 250 mL culture. In comparison, isolation of HydA1 from its native host requires 8 L of culture and multiple purification steps to produce enough hydrogenase for one IR spectroscopic measurement.

Materials and Methods

[FeFe] Hydrogenase and Maturase Expression Constructs The C. reinhardtii hydA1 and C. pasteurianum hydA genes were used for expression of the HydA1 and CpI [FeFe] hydrogenases, respectively. Both genes were previously codon-optimized for expression in E. coli. The coding sequencing for a C-terminal Strep-tag II® extension (IBA GmbH) with a two residue linker (5'-SAWSHPQFEK-3') was added by PCR amplifying the hydrogenase genes from the plasmids pY71 shydA1* and pK7 shydA [31]. PCR products were then cloned into the pET-21(b) expression vector (Novagen). The vector pACYCDuet-1-hydGX-hydEF was used for expression of the S. oneidensis [FeFe] hydrogenase maturases HydE, HydF, and HydG. Multiple cloning sites I and II contain the hydGX and hydEF nucleotide sequences, respectively. The hydX sequence (Accession code AAN56899) is a part of the S. oneidensis [FeFe] hydrogenase operon and encodes a soluble protein with no identified functions. The petF gene from Synechocystis sp. PCC 6803 was PCR amplified from the pK7 vector and cloned into the pET-21(b) plasmid. All expression constructs were confirmed by DNA sequencing and transformed into the E. coli strains BL21 (DE3) (Novagen) and BL21(DE3) ΔiscR by selection with the appropriate antibiotics.

Recombinant Expression and Purification of Active Hydrogenase. E. coli strains BL21(DE3) and BL21(DE3) ΔiscR contained the pACYCDuet-1-hydGX-hydEF plasmid and one of the two pET-21(b) hydrogenase plasmids. Cells were grown in LB Miller growth medium supplemented with kanamycin (40 $mg \cdot L^{-1}$), chloramphenicol (25 $mg \cdot L^{-1}$), ampicillin (100 $mg \cdot L^{-1}$), 0.5% w/v glucose (~25 mM), and 100 mM MOPS/NaOH (final pH of medium was 7.4). The ΔiscR strain contains a chromosomal substitution of the iscR gene with another gene conferring resistance to kanamycin. 10-50 mL cultures were grown for investigating the effects of cell strains and substrates, while 50-250 mL cultures were grown for hydrogenase purification work. 331 Initially, all cultures were grown aerobically at 25° C. until an $OD_{600}$ of 0.3-0.5. They were then moved into an anaerobic glove box (Coy Laboratory Products) containing 98% $N_2$ and 2% $H_2$ prior to IPTG-based T7 RNA polymerase induction and heterologous protein expression. While ferric ammonium citrate (2 mM) was added to the growth medium prior to inoculation, both cysteine (2 mM) and sodium fumarate (25 mM) were added with IPTG (0.5 mM) within the anaerobic glove box. Cultures were sealed and incubated at 25° C. for 16-24 hours following induction.

For investigating media formulations and protein expression by different strains, cells (1 mL of culture) were pelleted at 4,000×g and resuspended in 100 μL of anaerobic Bug-Buster® Master Mix lysis solution (Novagen) containing an additional 25 mM Tris/HCl (pH 8.0), 25 mM KCl, 3 mM sodium dithionite (DTH), 1 mM dithiothreitol (DTT), 2% v/v glycerol, 0.1% v/v Tween 20, 0.2 mM phenylmethylsulfonyl fluoride (PMSF), and 2 μM resazurin as an oxygen indicator. After cell lysis (incubation at 25° C. for 20 min), lysates were clarified by centrifugation at 14,000×g. Hydrogenase activities in cell lysates were measured using the methyl viologen reduction assay described below. Total protein content of lysates was determined using a commercial assay (Bio-Rad) based on the method of Bradford, and the extent of heterologous protein expression was visualized using polyacrylamide gel electrophoresis with SDS-PAGE gels (Invitrogen).

Hydrogenase purifications were carried out while maintaining strict anaerobic conditions.

After centrifugation and lysis as described above, approximately 1 mL of Strep-Tactin® Superflow® high capacity resin (IBA GmbH) was used per 50 mL of cell culture for purification. Wash and elution buffers contained the above lysis buffer additives excluding the BugBuster Master Mix and PMSF, and active hydrogenase was eluted with 2.5 mM D-desthiobiotin. Elution fractions were evaluated for active hydrogenase using the methyl viologen reduction assay, and fractions with high activity were pooled. Protein concentrations were measured with the Bradford assay, and hydrogenase iron content was measured using a ferrozine-based colorimetric assay. Hydrogenase samples for IR spectroscopic studies were anaerobically concentrated to ~100 μM using a 10 mL stirred cell and a 5 kD MWCO membrane (Amicon). Hydrogenase samples were not frozen prior to characterization and spectroscopic analysis.

Hydrogenase Activity Assays. Hydrogenase activities were measured at 37° C. in both the $H_2$ consumption and $H_2$ evolution directions using methods previously described. Generally, 1-25 ng of hydrogenase was tested. $H_2$ uptake was quantified with a methyl viologen reduction assay. 200 μL assay solutions contained 50 mM Tris/HCl (pH 8.0) and 2 mM methyl viologen. Absorbance was measured at 578 nm for 1-2 min following addition of lysate or purified hydrogenase. Methyl viologen reduction rates were adjusted by subtracting background activities, which were generally less than 1% of the hydrogenase activities. An extinction coefficient for reduced methyl viologen of 9.78 $mM^{-1} \cdot cm_{-1}$ was used to calculate $H_2$ oxidation rates, in which 2 moles of methyl viologen are reduced per mole of $H_2$ consumed. Hydrogen production was quantified using DTH-reduced methyl viologen (5 mM) or the ferredoxin PetF from Synechocystis (50 μM) as the electron donating substrate. 9.5 mL glass vials contained 1 mL of 100 mM MOPS/KOH buffer (pH 6.8), 100 mM KCl, 25 mM DTH, and either methyl viologen or ferredoxin. Upon hydrogenase addition, vials were sealed and the headspace was sparged with 100% $N_2$ for 2 min. $H_2$ quantities in the headspace were then quantified after 15-30 min of incubation using a ShinCarbon ST 100/120 mesh column (Resteck) with a Hewlett Packard 6890 gas chromatograph (Hewlett Packard). For PetF ferredoxin production, the petF gene from Synechocystis sp. PCC 6803 was first cloned from the pK7 plasmid into the pET-21(b) vector, and subsequently transformed into BL21(DE3) ΔiscR. Both PetF expression and purification using ammonium sulfate precipitation followed by anion exchange chromatography were carried out as previously described.

Fourier Transform IR Spectroscopy. Infrared spectra were measured using a Bruker IFS/66s FTIR spectrometer interfaced to a home-built stopped-flow drive system. The IR sample cuvette and drive system were maintained inside an anaerobic chamber ($O_2$<1.1 ppm) as previously described. The sample cuvette was maintained at 25° C. with a calibrated path length of 47.6 μm. For IR spectroscopic measurements, one drive syringe contained the protein sample. A second syringe contained either the elution buffer without any protein or buffer saturated with exogenous carbon monoxide. Spectra were measured at 4 $cm^{-1}$ resolution from 1000 sample scans, and the average spectrum was improved with a background correction.

Example 2

As described in Example 1, fully active hydrogenases can be produced in a recombinant host cell. Even though these initial fermentation protocols were designed for low cell densities, they produced at least 10-fold more active hydrogenase per liter than had ever before been reported. High level expression was also developed for the ferredoxins tested, one from E. coli and one from a Synechocystis strain. The latter coupled more effectively with the CpI hydrogenase and was used in further experiments. FNR is a complex enzyme that must incorporate an FAD cofactor; active FNR can be made via either an in vivo or in vitro protein translation. One skilled in the art will appreciate that further fermentation development will enable high level in vivo production of active FNR.

We have previously demonstrated high level ATP generation from oxidative phosphorylation in cell-free reactions and have also detected NADPH production. We decided to use purified enzymes for our initial attempts. In addition, we used only glucose-P dehydrogenase to represent the pentose phosphate pathway. This enzyme converts glucose-P to gluconic acid with the production of one molecule of NADPH.

The results shown in Table 1 indicate several points. The first column shows that initial attempts produced very little hydrogen. However, using higher protein concentrations produced disproportionate increases in hydrogen production rates and in the performance of the CpI enzyme (row 2). The last column indicates the potential activity of the $H_2$ase. In this case, the ferredoxin was maintained mostly in a reduced state using sodium dithionite as the reductant. The turnover number of 45 indicates that the maximum rates indicated by the other experiments are far below the $H_2$ase capacity. Although a turnover of 1.5 $sec^{-1}$ was the highest observed in these experiments, we believe that by using higher enzyme concentrations we can easily achieve CpI turnover rates of 5 $sec^{-1}$.

TABLE 1

Hydrogen Production from glucose 6-P and NADPH using purified proteins.

| | Aug. 8, 2009 | Feb. 9, 2010 | Feb. 16, 2010 | Mar. 17, 2010 | Mar. 17, 2010 | Mar. 24, 2010 | Mar. 24, 2010 | Dithionite |
|---|---|---|---|---|---|---|---|---|
| Volumetric Productivity[a] ($\mu$mole L$^{-1}$ hr$^{-1}$) | 0.011 | 76.5 | 1381 | 2996 | 5562 | 8633 | 2203 | $5.3 \times 10^6$ |
| Specific Rate ($\mu$mole min$^{-1}$ mg Cpl$^{-1}$) also = turnover number (sec$^{-1}$) | 0.008 | 0.0032 | 0.038 | 0.083 | 1.54 | 0.24 | 0.061 | 45 |
| Temperature (°C.) | 25 | 25 | 37 | 37 | 37 | 37 | 37 | 25 |
| [FNR] ($\mu$M) | 0.68[b] | 10[c] | 10[c] | 30[c] | 10[d] | 50[d] | 10[d] | 0 |
| [Fd] ($\mu$M) | 60 | 50 | 50 | 50 | 50 | 50 | 50 | 100 |
| [Cpl] ($\mu$M) | 0.01 | 10 | 10 | 10 | 1 | 10 | 10 | 0.033 |
| [NADPH] (mM) | 500 | 10 | 7 | 7 | 7 | 7 | [NADP$^+$] = 3 mM | [NaDTh] = 3 mM |
| Notes | | | | | stirred | stirred | stirred | |

[a][NaCl] = 21 mM, [Tris] = 37 mM, pH = 8, reactions initiated by addition of NADPH; all reactions included an NADPH regeneration system consisting of 3 mM G6P and 5 units of G6P dehydrogenase
[b]FNR Lot1
[c]FNR Lot2
[d]FNR Lot3

A simplified process flow diagram for the process is shown in FIG. 6, with the expected enzyme concentrations. These values were used with a Cpl turnover rate of 5 sec$^{-1}$ to assess the potential fuel value volumetric productivity for such a process. This compares very favorably to the fuel value volumetric productivity for a current glucose to ethanol process (10% ethanol after a 60 hour fermentation)

Thus, early results suggest glucose productivities at least 10 times greater than for current ethanol facilities. In addition, because of the efficiency of the glucose to hydrogen conversion and the ease in harvesting a gaseous product, it is believed that the energy conversion efficiency will also be better. Expansion of this technology to use xylose, the other major product from cellulosic biomass, is straightforward because xylose can be easily converted to ribose-P (another 5-carbon sugar) which is an intermediate in the pentose phosphate pathway and will also be converted to $CO_2$ to also provide NADPH for efficient hydrogen production.

The final process may require higher concentrations of NADP than will initially exist in the cell extracts, which will be produced using endogenous enzymes from niacin (an inexpensive vitamin) and from AMP released by an RNase from nucleic acids already in the cell extract. Iodoacetamide will be added to inactivate the normal glycolytic pathway (the EMP pathway) so that all of the glucose (and xylose) is processed through the pentose phosphate pathway.

Example 3

Hydrogen Production at High Volumetric Rates with the *Synechocystis* Ferredoxin The following purified proteins were used in this reaction: (1) FNR from *E. coli* at 50 $\mu$M, (2) [2Fe2S] ferredoxin from *Synechocystis* at 50 $\mu$M, (3) Cpl Hydrogenase from *Clostridium Pasteurianum* at 10 $\mu$M, and (4) glucose-6-phosphate dehydrogenase (G6PD) from yeast (Sigma-Aldrich G4134) at 0.05 units/$\mu$L. 3 mM G6P was added, the NaCl concentration was 21 mM, and reaction was buffered at pH 8 with 37 mM Tris. The G6PD and G6P constitute a NADPH regeneration system that functions to reduce NADP$^+$ to NADPH in order to maintain a constant concentration of NADPH and a low concentration of NADP$^+$.

The reaction was conducted with a 200 $\mu$L solution volume in a 2.5 mL glass vial. Reagents were added to the vial inside an anaerobic glove box. The vial was sealed with a septum and an aluminum crimp-cap, removed from the glovebox, and purged with nitrogen for 4 minutes to ensure the atmosphere was oxygen- and hydrogen-free. The reaction vial was pre-warmed to 37° C. in an incubator. NADPH was added to a final concentration of 7 mM to initiate the reaction, following which the vial was placed into the 37° C. incubator and shaken using a standard vortex mixer to facilitate mixing. The hydrogen concentration in the headspace was measured by removing 200 $\mu$L of the headspace gas with a glass syringe and injecting into an Agilent 6890 GC-TCD with a Restek Shincarbon column for hydrogen analysis. Hydrogen concentrations in the injected volume were determined from peak areas by comparing to calibration curves made from standards with known hydrogen concentrations.

Hydrogen evolution in the reaction was measured over the first 20 minutes at a rate of 8633 $\mu$mole H$_2$ L$^{-1}$ hr$^{-1}$; the Cpl hydrogenase turnover number was 0.24 sec$^{-1}$.

Example 4

Hydrogen Production at High Volumetric Rates with the *Clostridium Pasteurianum* Ferredoxin The following purified proteins were used in this reaction: (1) FNR from *E. coli* at 80 $\mu$M, (2) 2[4Fe4S] ferredoxin from *Clostridium Pasteurianum* at 160 $\mu$M, (3) Cpl Hydrogenase from *Clostridium Pasteurianum* at 2 $\mu$M, and (4) glucose-6-phosphate dehydrogenase (G6PD) from yeast (Sigma-Aldrich G4134) at 0.05 units/$\mu$L. 3 mM G6P was added, the salt concentration was 21 mM, and reaction was buffered at pH 8 with 37 mM Tris. The G6PD and G6P constitute a NADPH regeneration system that functions to reduce NADP$^+$ to NADPH in order to maintain a constant supply of NADPH and a low concentration of NADP+.

The reaction was conducted as described in example 1. Hydrogen evolution in the reaction was measured at a rate of 10,289 µmole $H_2$ $L^{-1}$ $hr^{-1}$; the Cpl hydrogenase turnover number was 1.43 $sec^{-1}$.

Example 5

Hydrogen Production from G6P and NADP+

In order to evaluate hydrogen production with the only source of electrons being G6P, a reaction was set up with only NADP+ added, relying solely on the NADPH regeneration system to supply electrons to FNR.

The following purified proteins were used in this reaction: (1) FNR from *E. coli* at 10 µM, (2) [2Fe2S] ferredoxin from *Synechocystis* at 50 µM, (3) Cpl Hydrogenase from *Clostridium Pasteurianum* at 10 µM, and (4) glucose-6-phosphate dehydrogenase (G6PD) from yeast (Sigma-Aldrich G4134) at 0.05 units/µL. 3 mM G6P was added, the NaCl concentration was 21 mM, and reaction was buffered at pH 8 with 37 mM Tris. The G6PD and G6P constitute a NADPH regeneration system that functions to reduce NADP+ to NADPH in order to maintain a constant supply of NADPH and a low concentration of NADP+.

The reaction was conducted as described in example 1. Hydrogen evolution in the reaction was measured at a rate of 2203 µmole $H_2$ $L^{-1}$ $hr^{-1}$; the Cpl hydrogenase turnover number was 0.06 $sec^{-1}$.

Example 6

Summary of Multiple Hydrogen Evolution Reactions

FIG. 7 illustrates the improvements in hydrogen production that we have observed. In our first experiments, using nanomolar concentration of enzymes, we observed extremely low rates of hydrogen production (column 1). By increasing the concentrations of the enzymes to 10-50 micromolar (enabled by improvements in overexpression and purification of the proteins that makeup the hydrogen production pathway), the hydrogen evolution rate was improved 7000 fold (column 2); a further 20-fold improvement was seen by increasing the temperature of the reaction from 25° C. to 37 C. (column 3). Continuing increases in FNR concentration and a change in procedure to keep the reaction solution well-mixed facilitated an increase in hydrogen evolution by another 5-fold (columns 4-5). As shown in the final two columns of the figure (and described in examples 1 and 2 above), rates of 8-10 millimoles of hydrogen per liter per hour are obtainable with 2 different ferredoxins, illustrating the robustness of the pathway. These results suggest that experimentation conducted by one skilled in the relevant art will identify optimal operating parameters of the invention as practical from a variety of different sources and with different compositions.

Example 7

Productivity Calculations and Comparison with Ethanol Productivities

Expecting that additional research will achieve a Cpl turnover rate of 5 $sec^{-1}$ and enzyme concentrations in the lysates of 144 µM for FNR, 833 µM for ferredoxin, and 86 µM for Cpl hydrogenase, we calculate a fuel value volumetric productivity of 0.40 $MJ$ $L^{-1}$ $hr^{-1}$. This compares very favorably with a biomass to ethanol productivity of 0.04 $MJ$ $L^{-1}$ $hr^{-1}$.

Example 8

Figure 8:
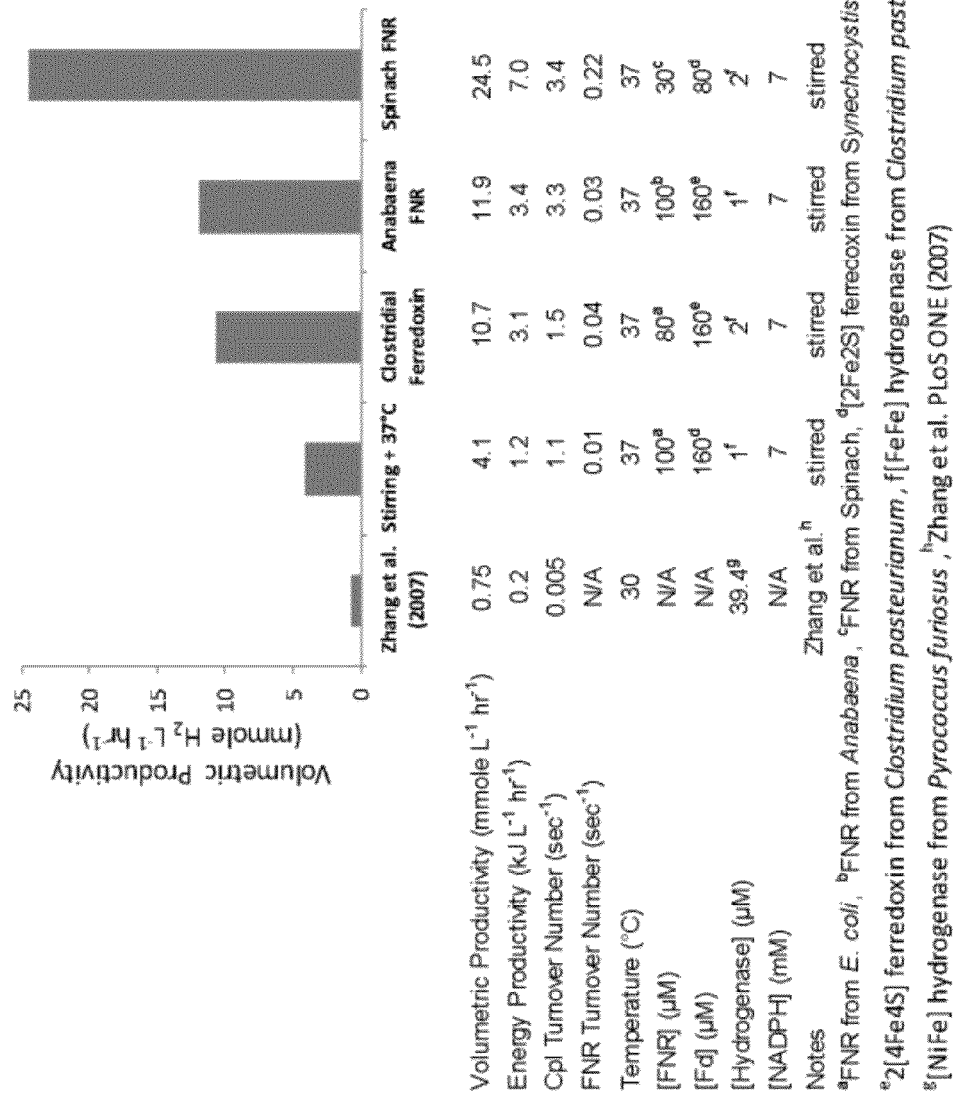
FIG. 8. Improvements in hydrogen productivity using the new pathway and corresponding conditions.

Summary of Multiple Hydrogen Evolution Reactions with Different FNRs and Fds FIG. 8 shows improvements in hydrogen productivity obtained by testing enzymes from different sources. In column 1, data previously published by Zhang et al. (Zhang 2007) are presented. In column 2, the best data from Smith 2011 is shown, using the FNR from *E. coli* and the ferredoxin from *Synechocystis*. In column 3, the ferredoxin from *Clostridium pasteurianum* (CpFd), which is the native electron donor for the hydrogenase, is used, giving a significant improvement in the rate of hydrogen production. Another improvement was obtained by changing to the FNR from *Anabaena* (AnFNR), as shown in column 4. Finally, using a commercially obtainable FNR from spinach gave another large improvement in the rate of hydrogen production, as shown in column 5.

Figure 9:
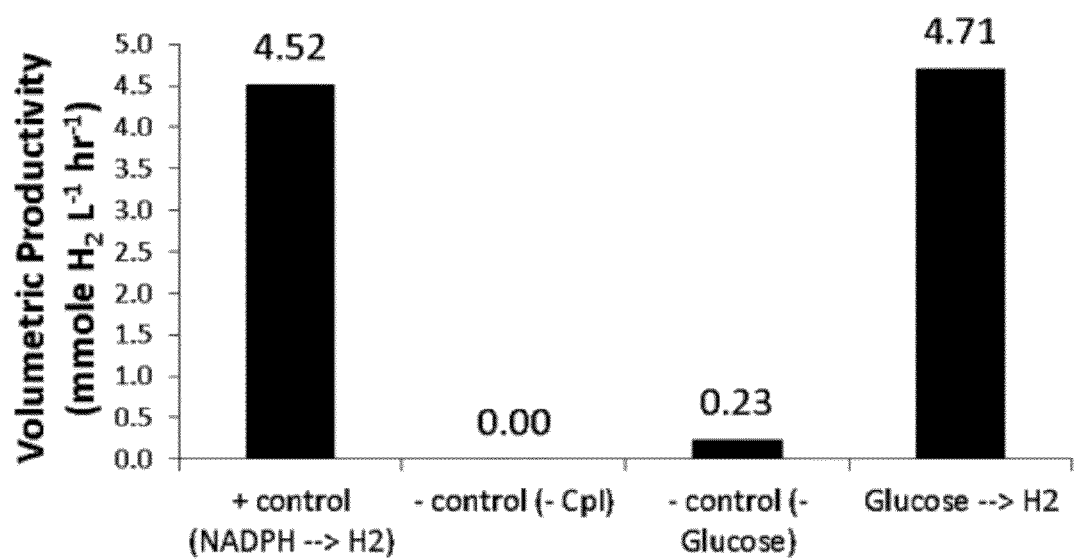

Following the same protocol for mixing and initiating reactions described in Smith et al., Generation of hydrogen from NADPH using an [FeFe] hydrogenase, International Journal of Hydrogen Energy (2011), doi:10.1016/j.ijhydene.2011.03.172, three purified enzymes, AnFNR, CpFd, and Cpl hydrogenase, were added to a micro-reactor containing the components listed in Table 2, which included a cell-lysate from an *E. coli* K-strain. Glucose was added last, to initiate the reaction and hydrogen production measured over time. Additionally, three control reactions were run to confirm that the hydrogen production was produced from glucose via the pentose phosphate pathway and the synthetic pathway. The volumetric productivities are presented in FIG. 9. These show that hydrogen production from glucose, with this synthetic pathway, matches that from NADPH (in the positive control); this indicates the feasibility of activating the pentose phosphate pathway. Further, the rate of hydrogen production from glucose, in a cell-lysate, matched the positive control (using purified enzymes, producing hydrogen from NADPH), suggesting that the pentose phosphate pathway is not rate limiting.

TABLE 2

| Reagent | Conc |
|---|---|
| AnFNR | 50 µM |
| CpFd | 80 µM |
| CpI H2ase | 1 µM |
| NADP+ | 1 mM |
| Glucose | 30 mM |
| PEP | 30 mM |
| Mg2+ | 10 mM |
| Hexokinase | 5 units |
| KPO4 Buffer | 20 mM |
| Cell-lysate | 55% |
| 100 µL Rxn | |

Example 7

Productivity Calculations and Comparison with Ethanol Productivities

With a Cpl turnover rate of 5 $sec^{-1}$ and the following enzyme concentrations in the lysates: 144 µM for FNR, 833 µM for ferredoxin, and 86 µM for Cpl hydrogenase; we calculate a potential fuel value volumetric productivity of 0.40 MJ L$^{-1}$ hr$^{-1}$. This compares very favorably with a biomass to ethanol productivity of 0.04 MJ L$^{-1}$ hr$^{-1}$.

What is claimed is:

1. A method of synthesizing molecular hydrogen (H$_2$) from a sugar, the method comprising:
   combining in a cell-free reaction mixture:
   (a) enzymes
      (i) active [FeFe] hydrogenase;
      (ii) ferredoxin; and
      (iii) ferredoxin-NADP-reductase (FNR);
   (b) microbial cell lysate;
   (c) sugar at a concentration of from about 1 to about 1000 mM;
   (d) a source of NAD at a concentration of from 0.1 mM to 1 mM;
   (e) an agent to inactivate endogenous microbial cell glycolytic pathway; and
   incubating the reaction for a period of time sufficient to produce H$_2$, wherein fuel value productivity is at least 0.1 MJ L$^{-1}$ hr$^{-1}$.

2. The method of claim 1, wherein the sugar is a monosaccharide.

3. The method of claim 2, wherein the monosaccharide is glucose or fructose.

4. The method of claim 1, wherein the sugar is a polysaccharide.

5. The method of claim 1, wherein one or more of the enzymes are synthesized by an *Escherichia coli* (*E. coli*) cell genetically modified by introduction of an expression vector comprising a genetic sequence encoding exogenous [FeFe] hydrogenase; ferredoxin; or ferredoxin-NADP-reductase (FNR), which genetic sequence is operably linked to a promoter, wherein the cell is cultured in nutrient media for inducing expression from the promoter, wherein the [FeFe] hydrogenase and ferredoxin are obtained from *Clostridium pasteurianum*.

6. The method of claim 5, wherein the [FeFe] hydrogenase and ferredoxin are synthesized in a single cell.

7. The method of claim 5, wherein the genetically modified (*E. coli*) cell is lysed to provide the microbial cell lysate of the reaction mixture.

8. The method of claim 6, wherein ferredoxin-NADP-reductase (FNR) is not synthesized in a cell with [FeFe] hydrogenase and ferredoxin.

9. The method of claim 1, wherein the microbial cell lysate is (*E. coli*).

10. The method of claim 1, wherein the agent is iodoacetamide at a concentration of from 10 to 50 μM.

11. A reaction mixture that produces molecular hydrogen (H$_2$) from a sugar, where the reaction mixture comprises:
   (a) enzymes
      (i) active [FeFe] hydrogenase;
      (ii) ferredoxin; and
      (iii) ferredoxin-NADP-reductase (FNR);
   (b) microbial cell lysate;
   (c) sugar at a concentration of from about 1 to about 1000 mM
   (d) a source of NAD at a concentration of from 0.1 mM to 1 mM;
   (e) iodoacetamide at a concentration of from 10 to 50 μM.

* * * * *